United States Patent [19]

Souma

[11] Patent Number: 5,144,956
[45] Date of Patent: Sep. 8, 1992

[54] ELECTRONIC SPHYGMOMANOMETER

[75] Inventor: Takahiro Souma, Kanagawa, Japan

[73] Assignee: Terumo Kabushiki Kaisha, Tokyo, Japan

[21] Appl. No.: 501,151

[22] Filed: Mar. 29, 1990

[30] Foreign Application Priority Data

May 24, 1989 [JP] Japan .................................. 1-128692

[51] Int. Cl.⁵ .................................................. A61B 5/02
[52] U.S. Cl. ...................................... 128/682; 128/667
[58] Field of Search ............... 128/672, 680, 681, 685, 128/67.7, 686, 687, 691

[56] References Cited

U.S. PATENT DOCUMENTS 3,527,204  9/1970  Lem et al. .
4,210,154  7/1980  Klein ..................................... 128/686
4,800,892  1/1989  Perry et al. ........................... 128/677
5,003,981  4/1991  Kankkunen et al. ................ 128/677

FOREIGN PATENT DOCUMENTS

0122123A3  10/1984  European Pat. Off. .
0197302A3  10/1986  European Pat. Off. .

Primary Examiner—Peter A. Aschenbrenner
Attorney, Agent, or Firm—Frishauf, Holtz, Goodman & Woodward

[57] ABSTRACT

An electronic sphygmomanometer measures blood pressure while deflating or inflating a cuff. Cuff pressurization is constant, irrespective of cuff size, up to about 10 mmHg. When this value is exceeded, supply of air to the cuff is controlled in accordance with the cuff size. The decision regarding the cuff size is made by reading in the size from a designating switch. The cuff pressure sampling period during inflation is made shorter than that during deflation.

6 Claims, 5 Drawing Sheets

ELECTRONIC SPHYGMOMANOMETER

BACKGROUND OF THE INVENTION

1. Field of the Invention

This invention relates to an electronic sphygmomanometer capable of feeding air in conformity with cuff size.

2. Description of the Prior Art

In order to inflate the cuff in an electronic sphygmomanometer, the conventional practice is to supply the cuff with compressed air using a surge tank or to supply the cuff with air in the same way irrespective of cuff size by means of a pump capable of being driven by a small internal battery. However, it is difficult to prevent overshoot in the former and difficult to obtain a precise pressure increase in the latter.

SUMMARY OF THE INVENTION

An object of the present invention is to provide an electronic sphygmomanometer in which overshoot can be prevented and a more precise pressure increase obtained.

Another object of the present invention is to provide an electronic sphygmomanometer of the type having a mechanism which interrupts a pressure increase while the increase is in progress and adjusts the gain at which Korotkoff sounds are detected, wherein the sphygmomanometer satisfies the requirement of a more precise adjustment-point pressure.

A further object of the present invention is to provide an electronic sphygmomanometer capable of shortening pressurization time and of improving the efficiency of memory utilization.

According to the present invention, the foregoing objects are attained by providing an electronic sphygmomanometer for measuring blood pressure while inflating or deflating a cuff, comprising discriminating means for discriminating the size of the cuff attached, measuring means for measuring pressure in the cuff attached, and pressurization control means for controlling supply of air to the cuff, in conformity with the size of the cuff discriminated by the discriminating means, when the measuring means determines that cuff pressure has been increased up to a set up level which is 20-30 mmHg higher than systolic pressure.

The pressurization control means executes control so as to supply air at a rapid rate while cuff pressure is being increased up to, say, approximately 10 mmHg, after which the supply of air is controlled in dependence upon the discriminated cuff size.

The discriminating means comprises a switch for designating cuff size.

Further, the foregoing objects are attained by providing an electronic sphygmomanometer for measuring blood pressure while deflating or inflating a cuff, comprising discriminating means for discriminating the size of the cuff attached, measuring means for measuring pressure in the cuff attached, pressurization control means for controlling supply of air to the cuff, in conformity with the size of the cuff discriminated by the discriminating means, when the measuring means determines that cuff pressure has been increased up to a set up a level which is 20-30 mmHg higher than systolic pressure, period setting means for setting a cuff pressure sampling period, and sampling period varying means for controlling the period setting means to make the sampling period at cuff inflation shorter in comparison with the sampling period at cuff deflation.

Further, the foregoing objects are attained by providing an electronic sphygmomanometer for measuring blood pressure while deflating or inflating a cuff, comprising measuring means for measuring pressure in the attached cuff, period setting means for setting a cuff pressure sampling period, and sampling period varying means for controlling the period setting means to make the sampling period at cuff inflation shorter in comparison with the sampling period at deflation.

Other features and advantages of the present invention will be apparent from the following description taken in conjunction with the accompanying drawings, in which like reference characters designate the same or similar parts throughout the figures thereof.

DESCRIPTION OF PREFERRED EMBODIMENT

Figure 1:
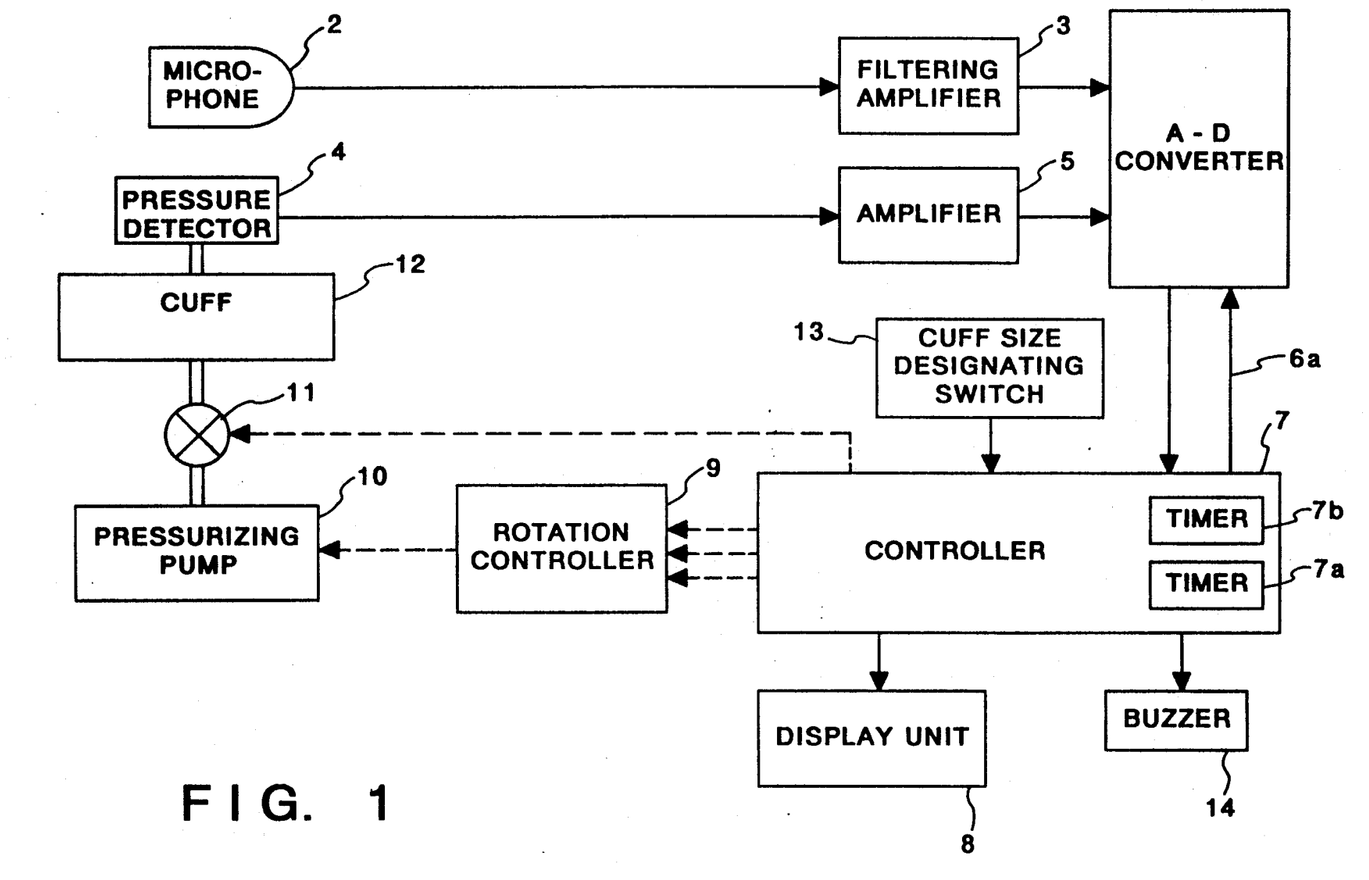
FIG. 1 is a block diagram illustrating the construction of an electronic sphygmomanometer embodying the present invention.

Fig. 1 is a block diagram illustrating the construction of an electronic sphygmomanometer embodying the present invention. As shown in FIG. 1, the electronic sphygmomanometer includes a microphone 2 attached to the lower edge of a cuff 12 so as to be near the elbow of the arm to which the cuff is affixed. The microphone 2 detects a signal indicative of blood flow and produces a signal indicative of the sound (Korotkoff or K sounds) of the blood flow. This signal is applied to a filtering amplifier 3, which selectively amplifies a required frequency component of the signal. Also included in the electronic sphygmomanometer is a pressure detector 4 mounted to the cuff 12 for detecting cuff pressure and producing an output signal indicative thereof, and an amplifier 5 for amplifying the output signal of the pressure detector 4.

Numeral 6 denotes an A/D converter which converts analog input signals, which are received from the filtering amplifier 3 and amplifier 5, into digital signals. Numeral 7 denotes a controller which receives the digital signals from the A-D converter 6, detects Korotkoff sounds from the blood-flow signal produced by the microphone 2, detects the pressure of the cuff 12 when the Korotkoff sounds are first detected, executes blood-pressure measurement processing, described below, and causes the results of processing, such as systolic and diastolic blood pressures, to be displayed on a display unit 8. The controller 7 which includes timers 7a and 7b, preferably comprises by a microprocessor unit on a single chip. The display unit 8 comprises an LCD for displaying the results of processing executed by the controller 7. A rotation controller 9 controls the rotational speed of a pressurizing pump 10 to supply the cuff 12 with compressed air in an amount commensurate with the size of the cuff attached. A discharge valve is connected between the pump 10 and the cuff 12.

Numeral 13 denotes a cuff size designating switch which the operator of the electronic sphygmomanometer uses to input cuff size by closing a switch L, M or S. A cuff of the small (S) size has dimensions of 38×88 mm, that of the medium (M) size dimensions of 53×120 mm, and that of the large (L) size dimensions of 70×53 mm.

The cuff size designating switch is not limited to one turned on and off by the operator, for it is possible to adopt a switch of the type wherein a cuff connector is provided with code information for identifying the cuff size, in which case the controller would be designed to automatically read the code. One way to achieve this would be to provide the connector with pins for forming a size code and code the pitch potentials to be high or low, thereby inputting the cuff size to the controller. Adopting such an arrangement makes it possible to prevent the occurrence of error caused by making an input from manual means.

Numeral 14 denotes a buzzer through which the operator can be provided with different warnings.

Figure 2A:
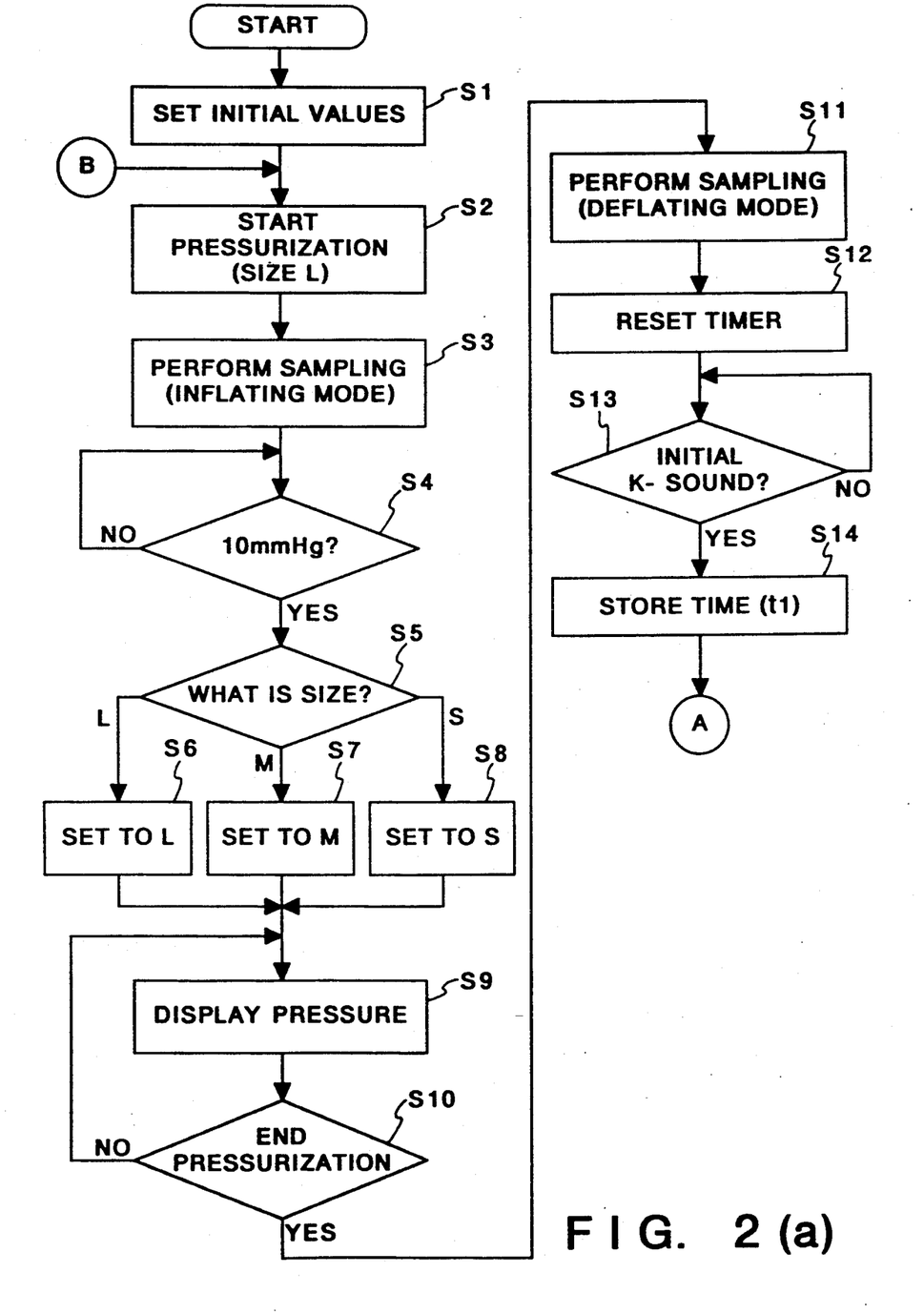
FIG. 2(a) and 2(b) are control flowcharts of the electronic sphygmomanometer shown in FIG. 1.
Figure 2B:
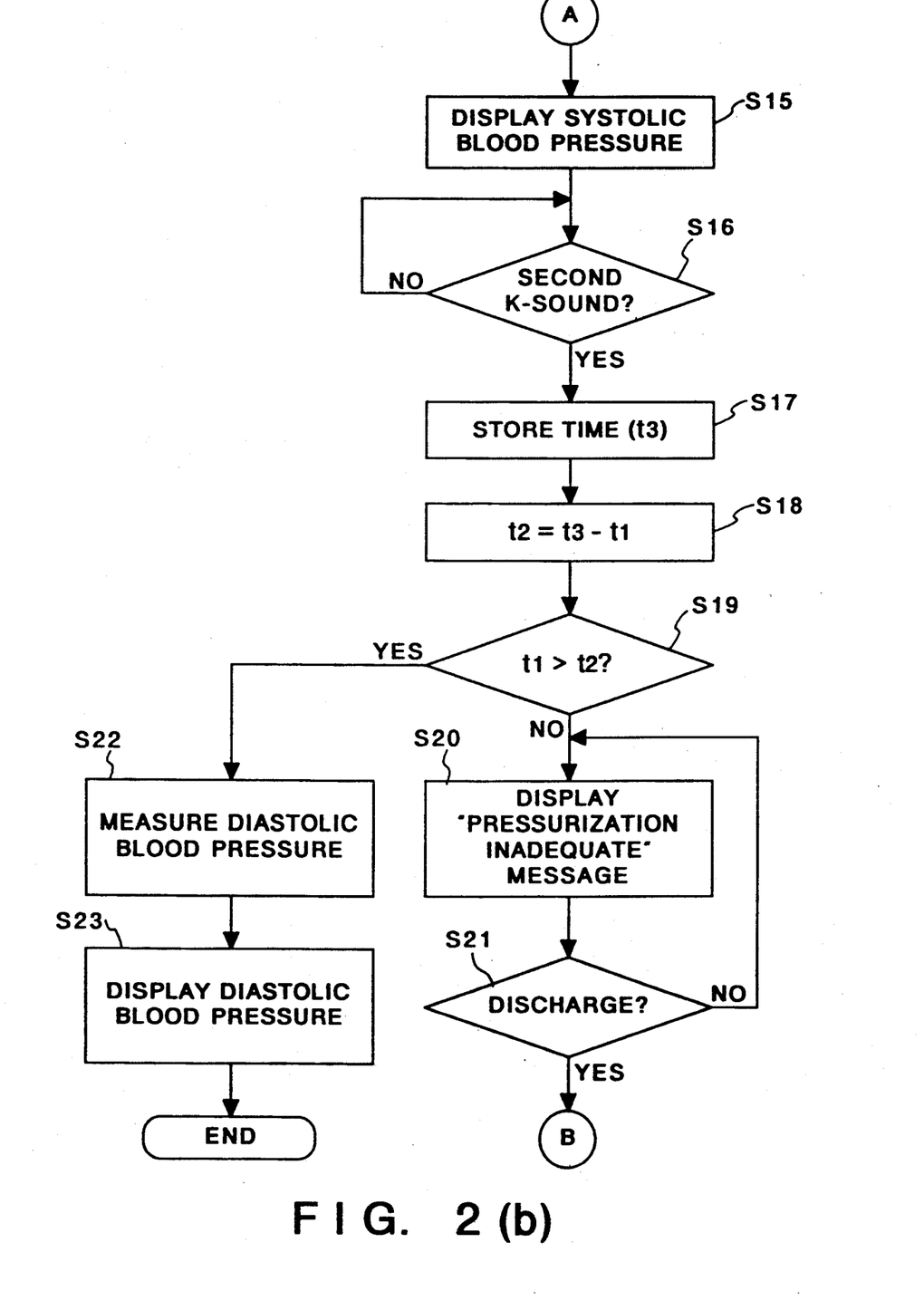

Control of blood pressure measurement in the electronic sphygmomanometer of the embodiment constructed as set forth above will now be described with reference to FIGS. 2(a), 2(b).

When electric power is introduced, the controller 7 checks the battery of the power supply and performs an initial setting operation such as a pressure zero-point adjustment at step S1. When the initial setting ends, preparations for blood pressure measurement are completed and the system waits for the start of measurement. When measurement of blood pressure begins, the program proceeds to step S2, at which blood pressure measurement is started upon preliminarily setting the rotation controller 9 to a pump rotational speed conforming to the large (L) cuff size.

At step S3, the timing signal generator 7b is set in such a manner that a conversion command signal is generated at a frequency of 250 Hz delivered to the converter 6. When it is determined at step S4 that sampled cuff pressure has been increased up to 10 mmHg, a size adjustment is executed based on the cuff size set in the cuff size setting switch 13 at step S5. In accordance with the set size, the rotational speed of the pressurizing pump is changed over to that for the L, M or S size at step S6, S7 or S8, cuff inflation continues in accordance with the rotational speed to which the changeover has been made.

Meanwhile, at step S7, cuff pressure is detected by the pressure detector 4 in accordance with the sampling frequency of the timing signal generator 7b, the detected pressure is converted into a digital signal by the A-D converter 6, and the controller 7 processes this signal and displays the results of processing on the display unit 8. Next, it is determined at step S10 whether cuff pressure has been increased up to a set up level. If the answer is YES, the program proceeds to step S11; if NO is the answer, inflation continues until a pressure is reached. The sampling frequency set in the timing signal generator 7b is changed to 2.5 Hz to increase the sampling interval at step S11. As a result of this operation, the amount of sampling data following the completion of pressurization is reduced. This makes it possible to raise the efficiency with which use is made of a working area in a RAM incorporated in the controller 7.

It should be noted that cuff inflation ends when a programmed set value and cuff pressure become equal.

Next, control proceeds to step S12, at which the timer 7a in controller 7 is reset and then started from zero. The controller 7 executes processing for recognizing Korotkoff sounds from the blood-flow sound signal produced by the microphone 2 and waits for recognition of the first beat of a Korotkoff sound (hereinafter referred to as a "K-sound") at step S13. When the first beat of the K-sound is detected, the program proceeds to step S14, at which the period of time ($t_1$) from the end of pressurization to the detection of the first K-sound is stored in a memory (not shown) of the controller 7. Next, at step S15, the detection output value of the pressure detector 4 at which the moment the first K-sound is detected is displayed on the display unit 8 as a systolic blood pressure value.

At step S16 the system waits for detection of the second beat of a K-sound. When this is detected, the program proceeds to step S17, at which the period of time ($t_3$) from the end of inflation to the detection of the second K-sound is stored in the memory of the controller 7. This is followed by a step S18, at which a K-sound occurrence interval ($t_2$) ($=t_3-t_1$) is calculated from the time ($t_3$) obtained at step S17 and the time ($t_1$) obtained at step S14. It is determined at step S19 whether $t_1 > t_2$ holds.

Generally, in order to measure systolic and diastolic blood pressures from K-sounds, the pressure of the cuff 12 is first gradually raised to a level of 20–30 mmHg higher than the systolic blood pressure. The occurrence of K-sounds is detected while the cuff 12 is gradually deflated (usually a rate of 2–3 mmHg every heartbeat). The cuff pressure value at which the first occurrence of the sound of blood flow is detected is adopted as the systolic blood pressure. As depressurization proceeds, the sound of blood flow accompanying this deflation gradually increases. There is a point at which this sound diminishes and a point at which it vanishes completely. The pressure value at the initial point where the sound diminishes or at the point where the sound vanishes is adopted as diastolic blood pressure.

Figure 3:
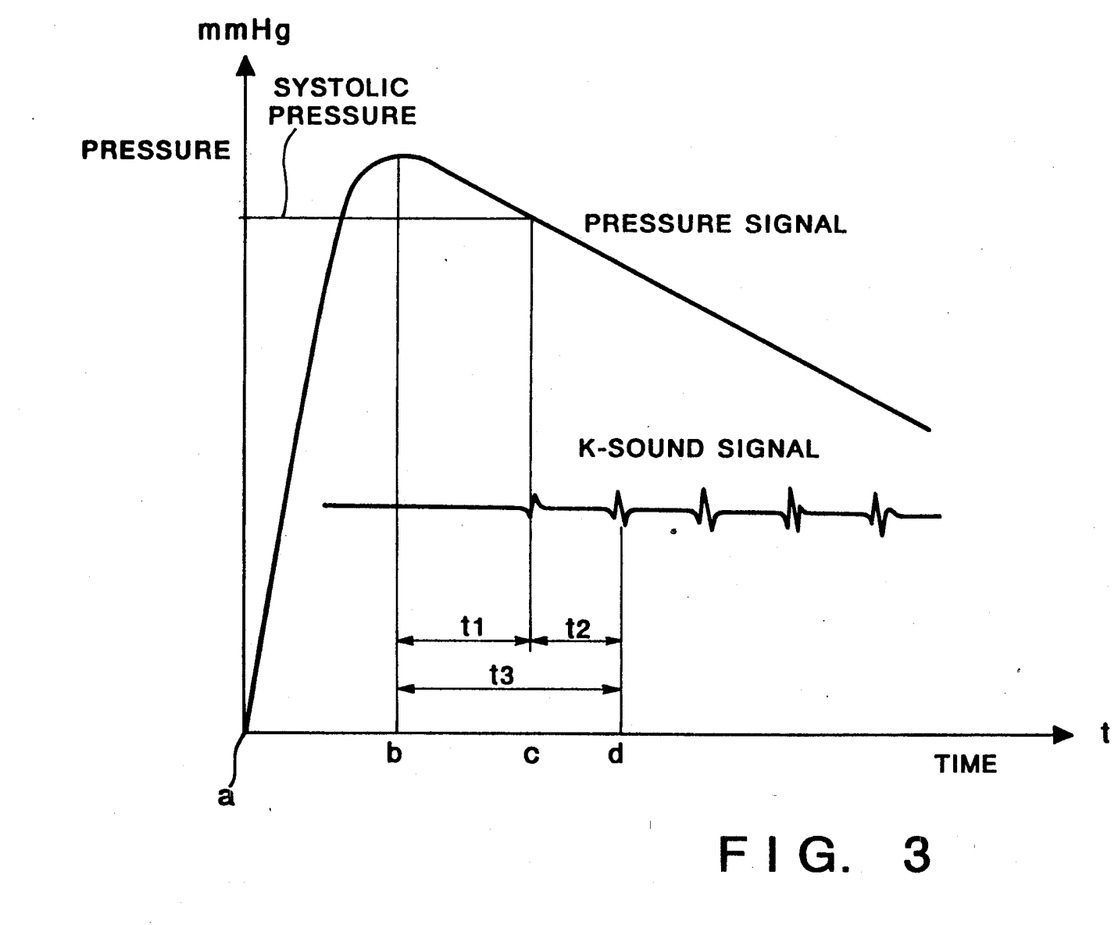
FIG. 3 is a time chart showing measurement timing of systolic blood pressure at which K sounds are detected.

The progress of inflation and deflation when measuring systolic blood pressure is shown in FIG. 3. When inflation starts at point a and cuff pressure is raised to the required value (point b), deflation is performed and the pressure value at point c, which is that at which the initial K-sound occurs, is adopted as the value of systolic blood pressure.

Accordingly, when the relation $t_1 \leq t_2$ is found to hold at step S19, this means that the initial inflating operation is unsatisfactory and the possibility is high that the operator has suspended inflation between the systolic and diastolic blood pressures. In such case, recognition of systolic blood pressure is erroneous. Accordingly, a message to the effect that inflation is inadequate is displayed on the display unit 8 at step S20, the buzzer 14 is sounded to issue and alarm, and discharge of air is requested. Discharge of air proceeds at step S21. When the value of pressure detected by the pressure detector 4 falls below a predetermined value and discharge is completed (YES at step S21), the program returns to step S2 to reestablish the measurement enable state. When $t_1 > t_2$ is found to hold at step S19, the pressure at which the first beat of the K-sounds has occurred is adopted as systolic blood pressure, then the program proceeds to step S22, at which processing is executed to measure diastolic blood pressure. The pressure value at the initial point where the K-sounds diminish or at the point where the K-sounds vanish is adopted as diastolic blood pressure. The value of diastolic blood pressure detected is displayed on the display unit 8 at step S23 and processing for measurement of blood pressure is terminated.

Since the amount of compressed air supplied is controlled in dependence upon cuff size by means of the above-described arrangement, it is possible to prevent overshoot, which occurs owing to a delay ascribable to the capacity component of the air circuitry.

Figure 4:
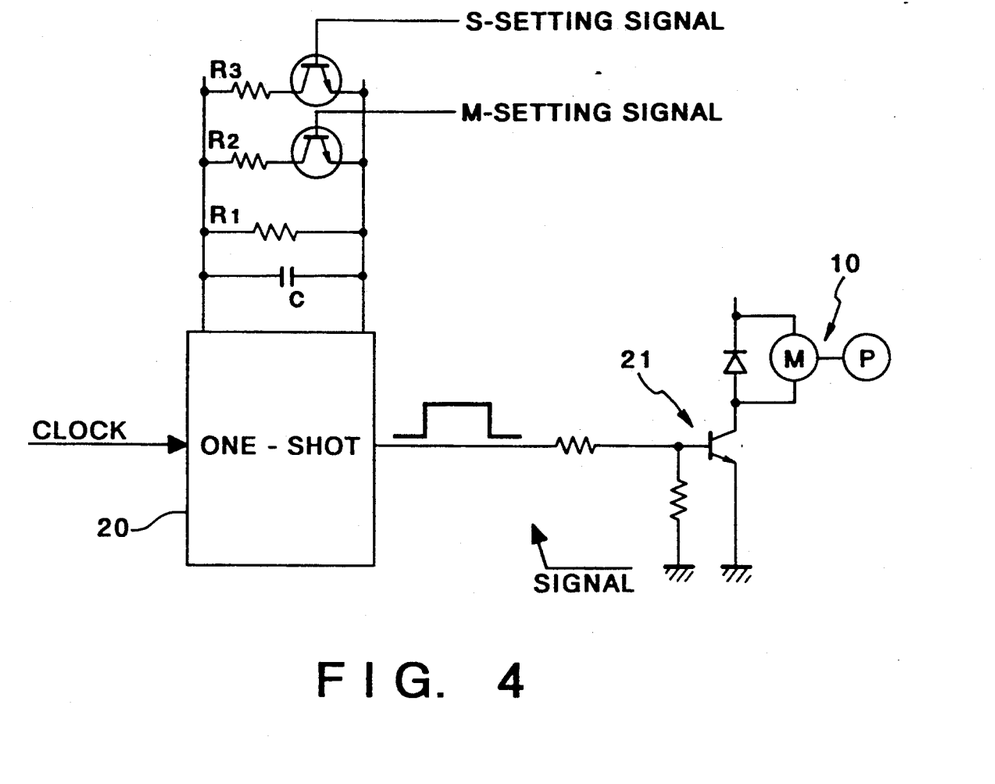
FIG. 4 is a circuit diagram showing the details of a rotation controller.

FIG. 4 is a circuit diagram illustrating an example of the rotation controller. The controller includes a one-shot multivibrator 20 which forms an output signal, the width of which corresponds to resistance and capacitance values, whenever a predetermined clock input is received from the controller 7. The values of resistors R1, R2, R3 are related as follows: R1>R2>R3, and it is arranged so that R1 and either R2 or R3 is selected at step S5. The width of the signal formed by the one-shot multivibrator 20 is set to a desired magnitude by the values of R1-R3. Specifically, large (L) is selected as the cuff size when signals for setting the small (S) and medium (M) sizes are at the low level. When the M-setting signal is high, the M size is selected. When the S-setting signal is high, the resistance value is minimized and the signal formed by the multivibrator has the minimum pulse width. A driver circuit 21 drives the pressurizing pump 10 in accordance with the signal width.

Figure 5:
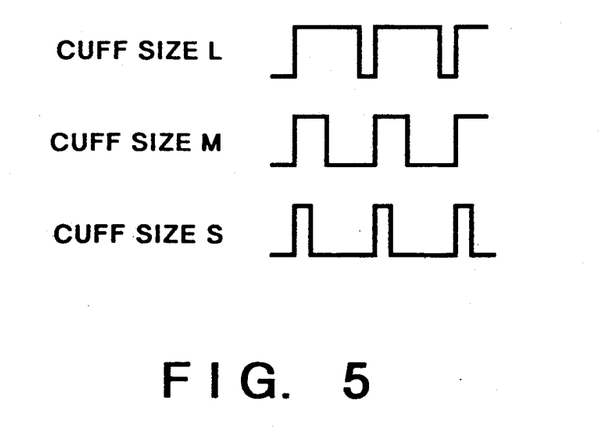
FIG. 5 is a waveform diagram showing the widths of signals, corresponding to cuff sizes, applied to a pressurizing pump.

FIG. 5 shows the signal widths formed by the one-shot multivibrator 20 when the cuff size is L, M and S.

Thus, in accordance with the embodiment described above, compressed air is supplied in conformity with cuff size. As a result, cuff pressure can be raised accurately to a set value of inflation necessary for measurement. In addition, since inflation to the predetermined value, is carried out rapidly irrespective of cuff size, the time needed for inflation can be reduced.

Furthermore, the period at which cuff inflation is monitored is set to be shorter than the period when the K sounds are detected while the deflating cuff is depressurized. This makes it possible to prevent collecting more than the necessary amount of sampling data at deflation. As a result, the working area of the RAM in the computer constituting the controller can be utilized more effectively.

Though measurement is performed during deflation in the foregoing embodiment, it goes without saying the measurement can be performed during inflation as well and that such an arrangement is covered by the present invention.

The present invention is advantageous in that it is possible to provide an electronic sphygmomanometer in which overshoot can be prevented and pressurization performed with greater accuracy. Another advantage is that the time needed for inflation can be shortened and memory can utilized more efficiently.

As many apparently widely different embodiments of the present invention can be made without departing from the spirit and scope thereof, it is to be understood that the invention is not limited to the specific embodiments thereof except as defined in the appended claims.

what is claimed is:

1. An electronic sphygmomanometer for measuring blood pressure while deflating or inflating a cuff which is attachable to a body part of a user, said electronic sphygmomanometer comprising:
   cuff size discriminating means for discriminating the size of the cuff when it is attached to a body part of a user;
   measuring means for measuring pressure in the attached cuff; and
   inflation control means for controlling a supply of air to the attached cuff, said inflation control means executing inflation control at least in first and second air supply modes;
   said inflation control means, in said first air supply mode, supplying air to the attached cuff at a rapid rate, independent of the cuff size discriminated by said cuff size discriminating means, while cuff pressure is being raised to a set pressure level; and
   said inflation control means, in said second air supply mode, supplying air to the attached cuff at a plurality of different air flow rates, varying in accordance with the cuff size discriminated by said cuff size discriminating means, up to a predetermined pressure level which is higher than said set pressure level.

2. The electronic sphygmomanometer according to claim 1, wherein set pressure level is approximately 10 mmHg.

3. The electronic sphygmomanometer according to claim 1, wherein said discriminating means comprises switch means for designating a cuff size.

4. The electronic sphygmomanometer according to claim 1, wherein said inflation control means, in said second air supply mode, supplies air to the attached cuff to increase the cuff pressure from said set pressure level to said predetermined pressure level.

5. The electronic sphygmomanometer according to claim 1, wherein said inflation control means further comprises:
   period setting means for setting a cuff pressure sampling period for setting time intervals at which cuff pressure is detected; and
   sampling period varying means for controlling said period setting means to make a sampling period at cuff inflation shorter in comparison with a sampling period at cuff deflation.

6. The electronic sphygmomanometer according to claim 1, wherein said sphygmomanometer measures blood pressure while deflating the cuff after the cuff is inflated to said predetermined pressure level.

* * * * *

UNITED STATES PATENT AND TRADEMARK OFFICE
CERTIFICATE OF CORRECTION

PATENT NO.  : 5,144,956
DATED       : September 8, 1992
INVENTOR(S) : SOUMA, Takahiro It is certified that error appears in the above-identified patent and that said Letters Patent is hereby corrected as shown below:

Replace Fig.1 with the one attached hereto.

Column 5, line 57, after "can", insert --be--.

Signed and Sealed this

Twenty-sixth Day of October, 1993

Attest:

BRUCE LEHMAN

Attesting Officer        Commissioner of Patents and Trademarks

FIG. 1